United States Patent [19]

Okegawa et al.

[11] Patent Number: 5,059,607
[45] Date of Patent: Oct. 22, 1991

[54] IMIDAZOLYL BENZISOQUINOLINES USEFUL AS 5-HT3 RECEPTOR ANTAGONISTS

[75] Inventors: Tadao Okegawa; Masonari Kawamura, both of Mishima, Japan

[73] Assignee: Ono-Pharmaceutical Co., Ltd., Osaka, Japan

[21] Appl. No.: 535,969

[22] Filed: Jun. 11, 1990

[30] Foreign Application Priority Data

Jun. 13, 1989 [JP] Japan .................. 1-148480

[51] Int. Cl.⁵ .................. C07D 221/10; A61K 31/435
[52] U.S. Cl. ..................... 514/290; 546/110
[58] Field of Search .................. 546/110; 514/290

[56] References Cited

FOREIGN PATENT DOCUMENTS 0247760 12/1987 European Pat. Off. .
336759 10/1989 European Pat. Off. .

OTHER PUBLICATIONS

Covey, Chemical Abstacts vol. 59, No. 3899b (1963).
North et al., Chemical Abstracts vol. 112, No. 198377a (1989).
Wolfbeis et al., Chemical Abstracts, vol. 95, No. 8, Aug. 24, 1981., abstract No. 63658c.
Carberas et al., Chemical Abstracts, vol. 108, No. 3, Jan. 18, 1988, abstract No. 21750h.
Nonomiya et al., Chemical Abstracts, vol. 86, No. 7, Feb. 14, 1977, abstract No. 43531s.

*Primary Examiner*—Mukund J. Shah
*Assistant Examiner*—Philip Patton
*Attorney, Agent, or Firm*—Stevens, Davis, Miller & Mosher

[57] ABSTRACT

A benzisoquinoline derivative of the formula:

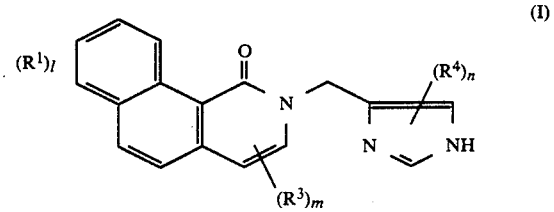

wherein
$R^1$ is hydrogen, C1-4 alkyl, C1-4 alkoxy, hydroxy or halogen;
$R^3$ is hydrogen or C1-4 alkyl;
$R^4$ is hydrogen or C1-6 alkyl;
1 is 1-6;
m is 1 or 2;
n is 1-3;

and non-toxic acid addition salts or hydrates thereof possessing an antagonistic activity against 5-HT3 receptor, and therefore being useful for the prevention and/or treatment of diseases induced when 5-HT acts on 5-HT3 receptor (especially vomiting induced by the administration of an anti-cancer agent).

3 Claims, No Drawings

IMIDAZOLYL BENZISOQUINOLINES USEFUL AS 5-HT₃ RECEPTOR ANTAGONISTS

SUMMARY

The present invention relates to novel benzisoquinoline derivatives.

More particularly, the present invention relates to:
i) A benzisoquinoline derivative of the formula:

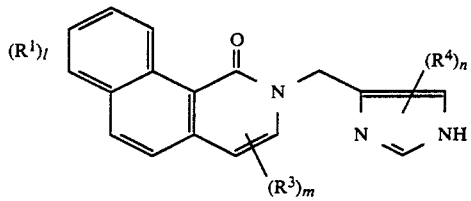

(wherein all of the symbols have the same meaning as defined hereafter) and non-toxic acid addition salts and hydrates thereof;
ii) processes for their preparation; and
iii) 5-HT₃ receptor antagonist containing them.

BACKGROUND

It is well known that 5HT (hydroxytryptamine, serotonin) is a neurotransmitter in the living body. Three types of receptors which are related to 5-HT are known, and they are called $5\text{-HT}_1$, $5\text{-HT}_2$ and $5\text{-HT}_3$ type receptors.

$5\text{-HT}_3$ receptors are widely distributed in the brain, heart and digestive canal, and 5-HT has an activity with respect to these receptors as a mediator.

It is confirmed that when 5-HT acts on $5\text{-HT}_3$ receptor at the peripheral nerve, pain and bardycardia are induced; and on the other hand, when 5-HT acts on $5\text{-HT}_3$ receptor at the central nerve, mental action e.g. emotions, appetite and memory, are induced. Further, 5-HT acts on $5\text{-HT}_3$ receptor at CTZ (chemoreceptor trigger zone) in the brain, nausea and vomiting being induced.

So it is thought that $5\text{-HT}_3$ receptor antagonist is useful for the prevention and treatment of central nerve diseases such as schizophrenia, corpulence, mania, anxiety, gastroenteric functional defects such as peptic ulcer, peptic esophagitis and migraine, vertigo, nausea and vomiting (especially vomiting induced by administration of an anti-cancer agent such as cisplatin).

It was known that large scale administration of Metocraplamide, which acts with side effects only, suppresses vomiting induced by an anti-cancer agent, and that other anti-vomiting agents are not effective.

RELATED ARTS

In these circumstances, development of $5\text{-HT}_3$ receptor antagonist is done. The following compounds are in the developing stage now.
(1) Code: ICS-205-930 (Sandoz)
(2) Code: BRL-24924 (Beecham)
(3) Code: GR-38032F (Glaxo)
(4) Code : MDL-72222 (Merrel Dow)

The compounds similar to the compounds of the present invention are, for example, compounds developed by Glaxo represented by (3).

These compounds are disclosed, for example, in the specification of

JP 60-214784 (i.e. GB 2153821)
JP 61-210083 (i.e. EP 191562)
JP 62-77382 (i.e. EP 219193)
JP 62-77381 (i.e. EP 210840)
JP 63-35570 (i.e. GB 2192885)
JP 63-211279 (i.e. GB 2202530)
JP 64-22870 (i.e. EP 297651)
JP 1-311082 (i.e. EP 338650)

For example, in the specification of Japanese Patent Kokai No. 60-214784, i.e. GB 2153821, the following compounds are disclosed.

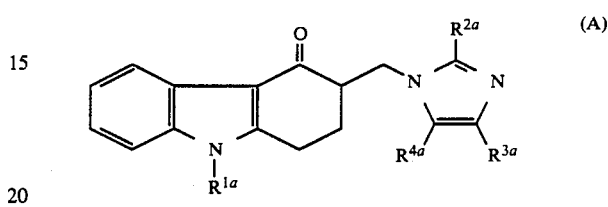

wherein $R^{1a}$ is hydrogen C1-10 alkyl, C3-7 cycloalkyl, C3-6 alkenyl, phenyl or phenyl-C1-3 alkyl, one of the group of $R^{2a}$, $R^{3a}$ and $R^{4a}$ is hydrogen, C1-6 alkyl, C3-7 cycloalkyl, C2-6 alkenyl or phenyl C1-3 alkyl, and the two other groups are, independently, hydrogen or C1-6 alkyl.

And JP 1-151578, i.e. EP 306323, discloses compounds having the structure similar to the compounds of the present invention.

The specification discloses that compounds of the formula:

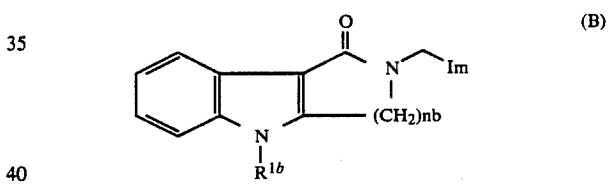

wherein Im represents an imidazolyl group of the formula:

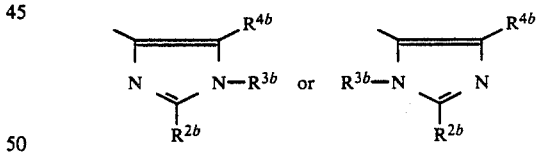

and $R^{1b}$ represents a hydrogen atom or a group selected from $C_{1-6}$alkyl, $C_{3-6}$alkenyl, $C_{3-10}$alkynyl, $C_{3-7}$cycloalkyl, $C_{3-7}$cycloalkyl$C_{1-4}$alkyl, phenyl, phenyl$C_{1-3}$alkyl, phenylmethoxymethyl, phenoxyethyl, phenoxymethyl, $-CO_2R^{5b}$, $-COR^{5b}$, $-COR^{5b}$, $-CONR^5R^6$ or $-SO_2R^{5b}$ (wherein $R^{5b}$ and $R^{6b}$, which may be the same or different, each represent a hydrogen atom, a $C_{1-6}$alkyl or $C_{3-7}$cycloalkyl group or a phenyl or phenyl$C_{1-4}$alkyl group, in which the phenyl group is optionally substituted by one or more $C_{1-4}$alkyl, $C_{1-4}$alkoxy or hydroxy groups or halogen atoms, with the proviso that $R^{5b}$ does not represent a hydrogen atom when $R^{1b}$ represents a group $-CO_2R^{5b}$ or $-SO_2R^{5b}$); one of the groups represented by $R^{2b}$, $R^{3b}$ and $R^{4b}$ is a hydrogen atom or a $C_{1-6}$alkyl, $C_{3-7}$cycloalkyl, $C_{3-6}$alkenyl, phenyl or phenyl$C_{1-3}$alkyl group, and each of the other two groups, which may be the same or different, represents a hydrogen atom or a $C_{1-6}$ group; $n^b$ represents 2 or 3; and physiologically acceptable salts and solvates thereof, are potent and selective antagonists of the effect of 5-HT on 5-HT$_3$ receptors.

PURPOSE

Widespread investigation has been carried out in order to discover compounds which have novel structure and possess an antagonistic activity on 5-HT$_3$ receptor. The present inventors have found that the above purpose can be accomplished by compounds of the present invention of the formula (I).

These compounds have a different structure compared to the compounds of the related arts. It is firstly confirmed that compounds replacing the carbazole skeleton (GR-38032F by Glaxo Ltd. etc.) by benzisoquinoline skeleton have a similar effect for the above purpose in the present invention. That is: the carbazole ring included in the compounds represented by the formula (A) has 6:5:6 ring members and has one nitrogen atom in the middle ring.

The $\gamma$-carboline ring included in the compounds of the formula (B) has also 6:5:6 ring members and has two nitrogen atoms in total, one atom in the middle ring and another atom in the right ring.

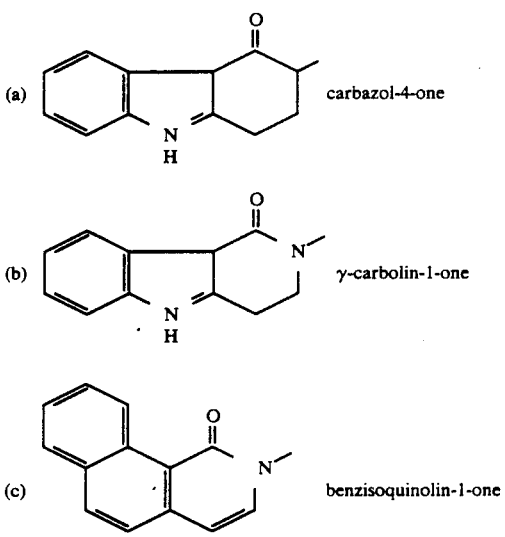

The compounds of the present invention of the formula (I) have a benz[1,2,h]isoquinoline ring, and this ring has 6:6:6 ring members and one nitrogen atom in the right ring. This ring structure is very different chemically in the fused rings of (a) and (b) mentioned above.

So it was not to be expected that the compounds of the present invention possess 5-HT$_3$ receptor antagonistic activity from a knowledge of the otherwise related art.

Eight applications showing compounds which have the carbazole ring structure represented by the formula (A) and one application of the compounds which have the $\gamma$-carboline ring structure of the formula (B) disclose that these compounds are useful as 5-HT$_3$ receptor antagonist.

All of the compounds mentioned above have a common structural feature. That is, one part of the fused ring is saturated, i.e. (a) the 1,2-position of the carbazole ring and (b) 3,4-position of the $\gamma$-carboline ring.

The fact suggests that those skilled in the art have hitherto considered that only compounds which are saturated in the particular position are effective as 5-HT$_3$ receptor antagonist.

With this background, the present inventors firstly found that the (c) benzisoquinoline ring compounds which have a 3,4-unsaturated double bond possess potent 5-HT$_3$ receptor antagonistic activity--contrary to all expectations.

Among the compounds of the present invention, it was confirmed that some compounds possess a stronger antagonistic activity against 5-HT$_3$ receptor than the carbazole type compounds and also lower toxicity.

DISCLOSURE OF THE INVENTION

The present invention relates to
i) a benzisoquinoline derivative of the formula:

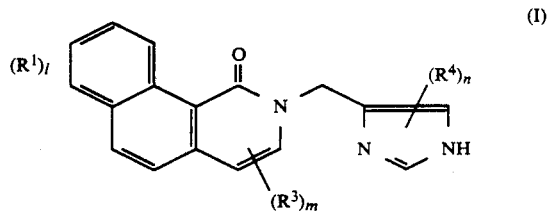

wherein
$R^1$ is hydrogen, C1-4 alkyl, C1-4 alkoxy, or halogen;
$R^3$ is hydrogen or C1-4 alkyl;
$R^4$ is hydrogen or C1-6 alkyl;
l is 1-6;
m is 1 or 2;
n is 1-3
and non-toxic acid-addition salts and hydrates thereof
ii) processes for their preparation; and
iii) 5-HT$_3$ receptor antagonist containing them.

In the formula (I), C1-4 alkyl represented by $R^1$ or $R^3$ means methyl, ethyl, propyl and butyl and isomers thereof In the formula (I), C1-6 alkyl represented by $R^4$ means methyl, ethyl, propyl, butyl, pentyl and hexyl and isomers thereof.

In the formula (I), C1-4 alkoxy represented by $R^1$ means methoxy, ethoxy, propoxy and butoxy and isomers thereof In the formula (I), halogen represented by $R^1$ means fluorine, chlorine, bromine, and iodine In the formula (I), among the groups represented by $R^1$, $R^3$ and $R^4$, especially preferable are hydrogen and methyl.

Throughout the present specification, all of the isomers are included unless otherwise specified. For example, alkyl or alkoxy includes straight or branched chains, and the present invention includes isomers generated by the existence of asymmetric carbon atoms e.g. the existence of branched alkyl.

ACID ADDITION SALTS

The compounds of formula (I) may be converted into the corresponding acid addition salts. Non-toxic and water-soluble salts are preferable. Suitable salts, for example are the following: salts of inorganic acids, e.g. hydrochloride, hydrobromide, sulphate, phosphate, nitrate, etc. Salts of organic acids, e.g. acetate, lactate, tartrate, fumarate, maleate, oxalate, citrate, benzoate, methanesulphonate, ethanesulphonate, benzenesulphonate, toluenesulphonate, isethioate, glucuronate, gluconate, etc. The hydrochloride is preferable.

Compounds of the general formula (I) or salts thereof may be converted into hydrates by per se conventional means.

PROCESS FOR THEIR PREPARATION

The compounds of the present invention of formula (I) may be prepared by N-alkylation of a compound of the formula:

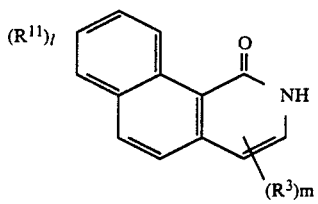
(II)

(wherein, $R^{11}$ is hydrogen, C1–4 alkyl, C1–4 alkoxy, protected hydroxy or halogen and the other symbols have the same meanings as defined hereinbefore) with a compound of the formula:

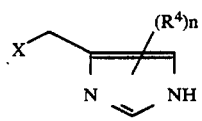
(III)

(wherein X is halogen, and the other symbols have the same meanings as defined hereinbefore) and when $R^1$ is protected hydroxy, and subjecting to hydrolysis under acidic conditions.

N-alkylation is a per se known reaction and may be carried out, for example, in a polar organic solvent (ethyl ether, THF, acetonitrile, DMF, HMPA etc.), in the presence of a base (sodium hydride, etc.).

The protecting group of the hydroxy group means a group which can be removed under acidic conditions; for example, methoxymethyl, tetrahydrofuranyl, tetrahydropyranyl, and 1-methoxy-ethyl.

Hydrolysis under acidic conditions is a per se known reaction and may be carried out, for example, in a water-miscible organic solvent (methanol, ethanol, THF, dioxane, etc.) using an aqueous solution of organic acid (acetic acid, p-toluenesulphonic acid, trichloroacetic acid, oxalic acid, etc.) or an aqueous solution of inorganic acid (hydrochloric acid, sulphuric acid, hydrofluoric acid, etc.) or mixtures thereof, at a temperature of from 0° C.–90° C.

The compounds of formula (II) may be prepared by following the reaction Scheme (A) below.

Each symbol represents the following meaning or as defined hereinbefore.

$R^{30}$, $R^{31}$: hydrogen or C1–4 alkyl
$R^{50}$: C1–4 alkyl

STARTING MATERIALS

Starting materials and reagents used in the present invention are known per se or may be prepared by known methods.

For example, a certain compound of the formula (III) wherein $(R^4)n$ is 5-methyl and X is chlorine is available in the market.

For example, a certain compound of the formula (IV) wherein $R^{30}$ is hydrogen and $(R^{11})_l$ is hydrogen is described in Beil 1, 401.

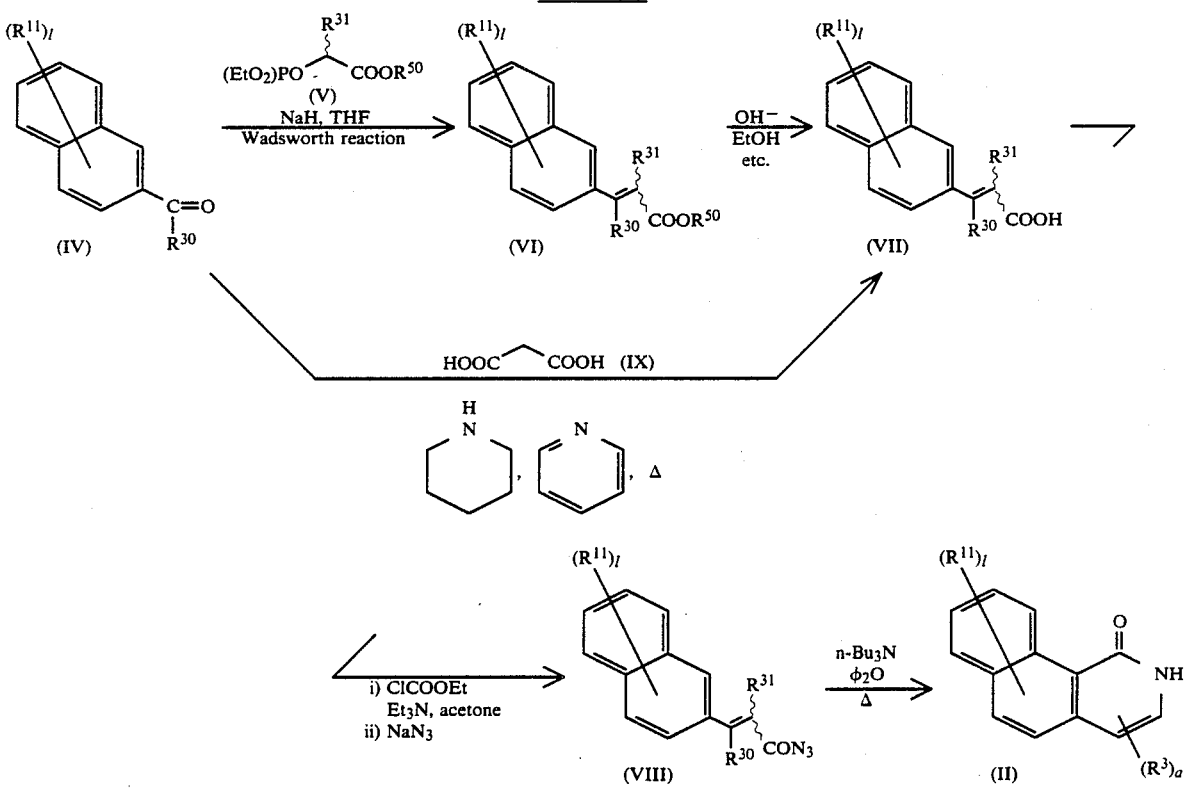
Scheme (A)

PHARMACOLOGICAL ACTIVITIES

The compounds of the present invention of formula (I) possess an antagonistic activity against 5-HT$_3$ receptors as described above, and for example, in a standard laboratory test, results in the following Table I are given.

TABLE I

| Example No. of the compound | An antagonistic activity against 5-HT$_3$ receptor in vivo in rats | |
|---|---|---|
| | IC$_{50}$ i.v. ($\mu$g/kg) | ID$_{50}$ i.d. ($\mu$g/kg) |
| 1 | 0.29 | 7.5 |
| 1(a) | 2.4 | — |
| 1(d) | 0.89 | — |
| 1(e) | 1.19 | — |
| 1(f) | 0.62 | — |
| 1(g) | 5.87 | — |

EXPERIMENTAL METHOD

Male Wister rat was urethane-anesthetized and fixed. Cannulas were inserted in the carotid artery and in the thigh vein as used for the recording of blood pressure and heart beat, and for the administration of the test compounds, respectively.

Several amounts of a compound of the present invention were administered from the vein or to the duodenum. 5-HT was administered rapidly to the vein, 2 mins. after administration of the compound of the present invention. The suppression effect of the compounds were confirmed by the measurement of the reflex bradycardia generated. (Nature 316, 126 (1985))

TOXICITY

On the other hand, tests confirmed that the toxicity of the compounds of the present invention is very low. Therefore, the compounds of the present invention may be considered to be sufficiently safe and suitable for pharmaceutical use.

For example, the value of acute toxicity (LD$_{50}$) of the compound prepared as in Example 1 was 94 mg/kg animal body weight by intravenous administration and more than 800 mg/kg animal body weight by oral administration in mice.

APPLICATION FOR PHARMACEUTICALS

It is thought that to block the activity of 5-HT$_3$ receptor is useful for the prevention and the treatment of central nerve diseases such as schizophrenia, corpulence, mania, anxiety, gastroenteric functional defect such as peptic ulcer, peptic esophagitis and migraine, vertigo, nausea, vomiting (especially vomiting induced by administration of an anti-cancer agent such as cisplatin) in animals including human beings, but especially in human beings.

The compounds of the present invention of formula (I) possess an antagonistic activity against 5-HT$_3$ receptor, shown in vivo in the experimental results above, so that they are expected to be adapted for the uses described previously.

For the purpose above described, the compounds of the present invention of formula (I), a non-toxic addition salt thereof, or a hydrate thereof, will normally be administered systemically or partially, usually by oral or parenteral administration.

The doses to be administered are determined depending upon age, body weight, symptoms, the desired therapeutic effect, the route of administration, the duration of the treatment, etc. In the human adult, the doses per person per dose are generally between 50 $\mu$g and 100 mg, preferably from 1 mg to 20 mg by oral administration, up to several times per day, and between 5 $\mu$g and 10 mg, preferably 500 $\mu$g to 10 mg by parenteral administration up to several times per day, or by continuous administration between 1 and 24 hrs per day from vein.

As mentioned above, the doses to be used depend upon various conditions. Therefore, there are cases in which doses lower than or greater than the ranges specified above may be used.

In the administration of the compounds of the present invention, one may use solid compositions, liquid compositions or other compositions for oral administration, as injections, liniments or suppositories, etc. for parenteral administration.

Solid compositions for oral administration include tablets, pills, capsules, dispersible powders, granules, etc.

Capsules include soft capsules and hard capsules.

Liquid compositions for oral administration include pharmaceutically acceptable-emulsions, solutions, suspensions, syrups and elixirs. Moreover such compositions may be employed with inert diluent(s) of the kinds commonly used (water, ethanol, etc.).

Injections for parenteral administration include sterile aqueous or non-aqueous solutions, suspensions and emulsions.

Other compositions for parenteral administration include liquids for external use, e.g. external solution, endermic liniments, ointments, suppositories for rectal administration, pessaries, etc.

EXAMPLES AND REFERENCE EXAMPLES

The following examples and reference examples further illustrate the present invention, but do not limit it.

The solvents in parentheses show the developing or eluting solvents and the ratio of the solvents used are by volume in chromatographic separations.

Unless otherwise specified, "IR" was measured by the KBr disk method.

The compounds of the present invention are named as benz[1,2-h]isoquinoline derivatives with numbering as shown in the following:

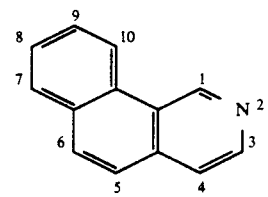

REFERENCE EXAMPLE 1

Synthesis of 3-(2-naphthyl)acrylic acid

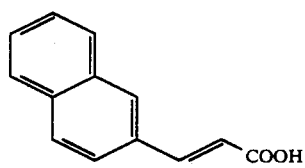

A solution of 2-naphthylaldehyde (3 g), piperidine (0.49 ml) and malonic acid (4.0 g) in pyridine (15 ml) was stirred for 2 hrs at 120° C. After cooling, the solution was acidified with conc. sulphuric acid. The solution was extracted with EtOAc. The oily layer was washed, dried, and evaporated to give the title compound (3.6 g) having the following physical data:
TLC: Rf 0.15 (EtOAc:hexane=1:1).

REFERENCE EXAMPLE 2

Synthesis of 3-(2-naphthyl)acryloyl azide

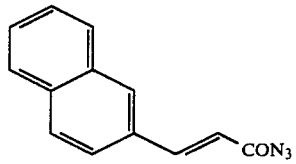

A solution of the compound prepared in Reference Example 1 (991 mg) and Et₃N (0.84 ml) in acetone (5 ml) was cooled with ice. Ethyl chloroformate (0.57 ml) was added dropwise to the solution. A solution of sodium azide (488 mg) in water (2 ml) was added dropwise to the solution. Acetone (5 ml) was added to the mixture. The solution was stirred for 1 hr. After reaction, solvent was removed from the solution The residue was poured into water. The mixture was extracted with methylene chloride. The oily layer was washed, dried and evaporated to give the title compound.

REFERENCE EXAMPLE 3

Synthesis of 1,2-dihydrobenz[1,2-h]isoquinolin-1-one

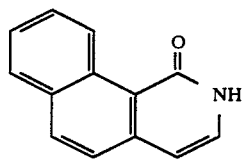

A solution of n-Bu₃N (1.3 ml) in diphenyl ether (5 ml) was heated at 230° C. A solution of the compound prepared in Reference Example 2 in diphenyl ether was added to the solution dropwise. After cooling, hexane was added to the reaction solution. The solids deposited were gathered by filtration. The solids were washed with hexane, and dried to give the title compound (655 mg) having the following physical data.
TLC: Rf 0.58 (chloroform:methanol=5:1).

EXAMPLE 1

Synthesis of 2-(5-methylimidazol-4-yl-methyl)-1,2-dihydrobenz[1,2-h]isoquinolin-1-one hydrochloride

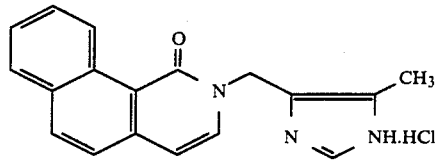

The compound prepared in Reference Example 3 (293 mg) was dissolved in DMF (4 ml). Sodium hydride (240 mg) was added to the solution. The mixture was stirred for 20 mins at room temperature. A suspension of 4-chloromethyl-5-methylimidazole hydrochloride (501 mg) in DMF (2 ml) was added to the solution The mixture was stirred for 40 mins at room temperature. The reaction mixture was poured into ice water. The mixture was extracted with chloroform. The oily layer was dried and evaporated. The residue was purified by column chromatography on silica gel (chloroform:methanol=20:1) to give a pale yellow oil (204 mg). The oil was dissolved in methanol (2 ml), and 4N HCl-dioxane (2 ml) was added to the solution. The solution was evaporated. The residue was washed with diethyl ether, and dried to give the title compound (194 mg) having the following physical data.
TLC: Rf 0.38 (chloroform:methanol=5:1);
IR: ν 3087, 2992, 2823, 2755, 2652, 1653, 1611, 1547, 1478, 1425, 1382, 1243, 1137, 835, 745, 631, 517 cm⁻¹.

EXAMPLE 1(a) –1(g)

By the same method shown in Reference Examples 1 to 3 and by the same procedure of Example 1, the compounds having the physical data described in following Table II were given.

The compound shown in Example 1(f) was obtained by treating conc. HCl-MeOH before conversion into acid addition salt.

TABLE II

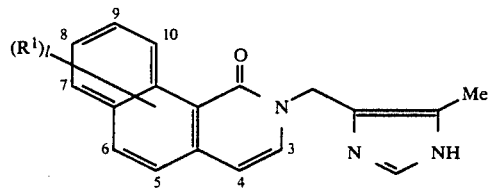

| Example No. | (R¹)ₗ | Name | TLC (Rf) | IR (ν cm⁻¹) |
|---|---|---|---|---|
| 1(a) | 5-MeO— | 2-(5-methylimidazol-4-ylmethyl)-5-methoxy-1,2-dihydrobenz[1,2-h]isoquinolin-1-one hydrochloride | 0.52 (CHCl₃:MeOH = 5:1) | 3008, 1654, 1613, 1553, 1503, 1463, 1380, 1292, 1243, 1175, 1115, 1052, 846, 811, 739 |
| 1(b) | 5-MeO— 7-MeO— | 2-(5-methylimidazol-4-ylmethyl)-5,7-dimethoxy-1,2-dihydrobenz[1,2-h]isoquinolin-1-one hydrochloride | 0.25 (CHCl₃:MeOH = 5:1) | 3396, 3004, 2904, 1656, 1603, 1505, 1468, 1276, 1254, 1242, 1105, 1060, 818, 761, 734 |
| 1(c) | 8-MeO— | 2-(5-methylimidazol-4-ylmethyl)-8-methoxy- | 0.57 (CHCl₃:MeOH = 5:1) | 2991, 2750, 1654, 1605, 1552, 1488, 1380, 1362, 1252, 1169, |

TABLE II-continued

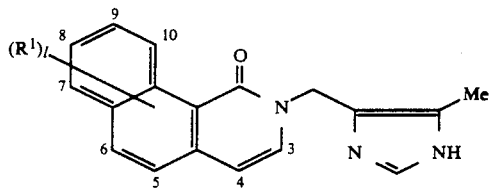

| Example No. | (R¹)ₗ | Name | TLC (Rf) | IR (ν cm⁻¹) |
|---|---|---|---|---|
| | | 1,2-dihydrobenz[1,2-h]isoquinolin-1-one hydrochloride | | 1133, 1045, 850, 836 |
| 1(d) | 6-Me— | 2-(5-methylimidazol-4-ylmethyl)-6-methyl-1,2-dihydrobenz[1,2-h]isoquinolin-1-one hydrochloride | 0.3 (CHCl₃:MeOH = 10:1) | 2993, 2839, 2755, 2653, 1655, 1610, 1549, 1383, 1241, 882, 836, 759 |
| 1(e) | 5-Me— | 2-(5-methylimidazol-4-ylmethyl)-5-methyl-1,2-dihydrobenz[1,2-h]isoqionolin-1-one hydrochloride | 0.33 (CHCl₃:MeOH = 10:1) | 2980, 2810, 2739, 2647, 1655, 1602, 1443, 1375, 1241, 1213, 1175, 1023, 921, 865, 811, 755 |
| 1(f) | 5-HO— | 2-(5-methylimidazol-4-ylmethyl)-5-hydroxy-1,2-dihydrobenz[1,2-h]isoquinolin-1-one hydrochloride | 0.30 (CHCl₃:MeOH = 5:1) | 3156, 1650, 1616, 1581, 1448, 1337, 1240, 1177, 1154, 982, 846, 813, 744 |
| 1(g) | 6-Br— | 2-(5-methylimidazol-4-ylmethyl)-6-bromo-1,2-dihydrobenz[1,2-h]isoquinolin-1-one hydrochloride | 0.45 (CHCl₃:MeOH = 10:1) | 2992, 2838, 2753, 2654, 1665, 1609, 1586, 1545, 1479, 1402, 1240, 905 |

FORMULATION EXAMPLE 1

The following components were admixed by conventional methods and punched out to obtain 100 tablets each containing 20 mg of active ingredient.

| | | |
|---|---|---|
| 2-(5-methylimidazol-4-ylmethyl)-1,2 dihydrobenz[1,2-h]isoquinolin-1-one hydrochloride | 1.0 g | |
| Calcium cellulose glycolate (carboxymethylcellulose calcium; disintegrating agent) | 0.2 g | |
| Magnesium sterate (lubricating agent) | 0.1 g | |
| Lactose | 8.7 g | |

FORMULATION EXAMPLE 2

The following components were admixed in conventional manner. The solution was sterilized in conventional manner, placed in 1 ml portions into 5 ml ampoules and freeze-dried to obtain 100 ampoules each containing 2 mg of the active ingredient.

| | |
|---|---|
| 2-(5-methylimidazol-4-ylmethyl)-1,2-1,2-dihydrobenz[1,2-h]isoquinolin-1-one hydrochlorie | 0.2 g |
| Lactose | 2 g |
| Distilled water | 100 ml |

What is claimed is:

1. A benzisoquinoline derivative of the formula:

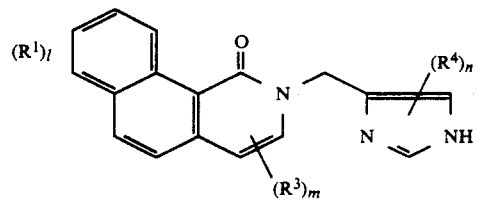

(I)

wherein
R¹ is hydrogen, C1–4 alkyl, C1'4 alkoxy, or halogen;
R³ is hydrogen or C1–4 alkyl;
R⁴ is hydrogen or C1–6 alkyl;
l is 1–6;
m is 1 or 2;
n is 1–3;
and non-toxic acid addition salts or hydrates thereof.

2. A method for the prevention and treatment of diseases induced when 5-hydroxytryptamine acts on 5-hydroxytryptamine 3 receptor, which comprises the administration of an effective amount of a benzisoquinoline derivative of the formula (I), non-toxic acid addition salts or hydrates thereof as defined in claim 1.

3. A pharmaceutical composition which comprises a benzisoquinoline derivative of the formula (I), and non-toxic acid addition salts or hydrates thereof, as defined in claim 1, in association with a pharmaceutically acceptable carrier or coating.

* * * * *